(12) United States Patent
Laureyn et al.

(10) Patent No.: US 7,955,883 B2
(45) Date of Patent: Jun. 7, 2011

(54) POLYMER REPLICATED INTERDIGITATED ELECTRODE ARRAY FOR (BIO) SENSING APPLICATIONS

(75) Inventors: Wim Laureyn, Leefdaal (BE); Jan Suls, Dworp (BE); Paul Jacobs, Lokeren (BE)

(73) Assignees: IMEC, Leuven (BE); Innogenetics, Gent (BE)

(*) Notice: Subject to any disclaimer, the term of this patent is extended or adjusted under 35 U.S.C. 154(b) by 243 days.

(21) Appl. No.: 12/089,528

(22) PCT Filed: Sep. 6, 2006

(86) PCT No.: PCT/EP2006/066069
§ 371 (c)(1),
(2), (4) Date: Mar. 11, 2009

(87) PCT Pub. No.: WO2007/042356
PCT Pub. Date: Apr. 19, 2007

(65) Prior Publication Data
US 2009/0221446 A1  Sep. 3, 2009

Related U.S. Application Data

(60) Provisional application No. 60/725,003, filed on Oct. 7, 2005.

(30) Foreign Application Priority Data

Oct. 7, 2005  (EP) .................................... 05109353

(51) Int. Cl.
*H01L 21/00* (2006.01)
*H01L 21/66* (2006.01)

(52) U.S. Cl. ... 438/49; 422/68.1; 422/82.01; 422/82.02; 429/19; 29/592; 29/592.1; 438/14; 438/17; 438/22; 438/23; 438/24; 438/48; 438/41; 438/44; 438/256; 438/361; 438/399; 438/400; 438/430; 438/478; 438/485; 438/641; 438/674

(58) Field of Classification Search .................. 429/19; 422/68.1, 82.01, 82.02; 29/592, 592.1; 438/14, 438/17, 22, 23, 24, 48, 49, 41, 44, 256, 361, 438/399, 400, 430, 478, 485, 641, 674
See application file for complete search history.

(56) References Cited

FOREIGN PATENT DOCUMENTS

| DE | 19950378 A1 | 5/2001 |
|---|---|---|
| EP | 0876601 B1 | 7/2004 |

OTHER PUBLICATIONS

European Search Report, European Patent Application EP05109353 dated Feb. 16, 2006.
(Continued)

*Primary Examiner* — Brian J Sines
(74) *Attorney, Agent, or Firm* — McDonnell Boehnen Hulbert & Berghoff LLP

(57) ABSTRACT

Interdigitated electrode arrays are very promising devices for multi-parameter (bio)sensing, for example the label-free detection of nucleic acid hybridization for diagnostic applications. The current disclosure provides an innovative method for the affordable manufacturing of polymer-based arrays of interdigitated electrodes with µm-dimensions. The method is based on a combination of an appropriate three-dimensional structure and a single and directional deposition of conductive material. The three-dimensional structure can be realized in a polymer material using a molding step, for which the molds are manufactured by electroplating as a reverse copy of a silicon master structure. In order to ensure sufficient electrical isolation and individual, but convenient, accessibility of the sensors in the array, the interdigitated electrode regions need to be complemented with specific features on the three-dimensional structure. Combined with the use of e.g. shadow masks in the deposition step, these features allow for the site-specific deposition of the conductive material. The technology described has the additional advantage to integrate highly miniaturized and arrayed electronics elements into polymer micro-fluidics technology, which leads to the affordable manufacturing of (bio)sensor arrays.

22 Claims, 18 Drawing Sheets

OTHER PUBLICATIONS

PCT International Search Report, PCT Application No. PCT/EP2006/066069, dated Mar. 1, 2007.
Sugawara, Akira et al., "Self-Organized Fe Nanowire Arrays Prepared by Shadow Deposition on NaCl(110) Templates", Applied Physics Letters, AIP, American Institute of Physics, vol. 70, No. 8, Feb. 24, 2007, pp. 1043-1045.
Van Gerwen, P. et al., "Cost Effective Realization of Nanoscaled Interdigitated Electrodes", Journal of Micromechanics and Microengineering, vol. 10, No. 3, Sep. 2000, pp. N1-N5.
Van Gerwen, Peter et al., "Nanoscaled Interdigitated Electrode Arrays for Biochemical Sensors", Sensors and Actuators, vol. 49, No. 1-2, Jun. 25, 1998, pp. 73-80.
PCT Written Opinion, PCT International Application No. PCT/EP2006/066069, dated Feb. 21, 2007.

POLYMER REPLICATED INTERDIGITATED ELECTRODE ARRAY FOR (BIO) SENSING APPLICATIONS

TECHNICAL FIELD

The present invention relates to the field of biosensors. An exemplary system according to the invention comprises an improved sensor comprising interdigitated electrodes for electronically detecting a binding reaction between molecules or between a pair of chemical substances. The present invention further comprises a new cost-effective fabrication method to produce this improved sensor. The (bio)sensor system may be used in the field of diagnostics in medical and non-medical applications.

BACKGROUND

Techniques and sensors for detecting molecules and specific substances such as peptides, enzymes, antigens, antibodies, oligonucleotides, DNA or RNA fragments in a sample solution are known in the art. In a specific class of sensors, use is made of the principle of measuring the impedance between two electrodes. The absence or presence of oligonucleotides, peptides/proteins, or antigens between the electrodes affects the permittivity and/or the conductivity between the electrodes.

As lithography and e-beam patterning are expensive, a new cost-effective approach was proposed in EP 0 876 601. An insulating substrate is patterned with a plurality of interspaced channels with submicron dimensions. Hills are located on this insulating substrate near the channels such that shadow zones are obtained upon non-orthogonal directional deposition of a conductive material thereby forming an impedimetric device. In J. Micromech. Microeng. 10 (2000), N1-N5, P. Van Gerwen et al propose an optimised design for this sensor, i.e. the hills are located at the end of the channels forming a shadow zone reaching part of the subsequent channel. This avoids electrical contact between adjacent electrode fingers and ensures the formation of interdigitated electrodes.

In EP 0 876 601 and J. Micromech. Microeng. 10 (2000), N1-N5, a sensor comprising interdigitated electrodes on an insulating substrate is described as well as a method for producing this sensor without lithography. To detect the presence or absence of molecules, the change of the impedance between interdigitated electrodes is measured. To increase the sensitivity various single sensors may be combined, possibly containing different probes for binding to different molecules. The different electrodes of these sensors are electrically isolated by microelectronics patterning techniques. This results in extra processing steps including expensive lithography.

AIM

It is an aim of the current invention to propose a method to produce sensors on an insulating substrate, whereby the electrical isolation between the electrodes within one sensor and between different sensors can be obtained without extra process steps.

SUMMARY

In a first aspect, a method to produce a sensor comprising at least 2 interdigitated electrodes is presented. This method, based on non-orthogonal directional deposition of a conductive material on an insulating substrate, comprises the following steps:

defining at least one electrode region on the insulating substrate, each having at least a first zone for forming a first electrode with first fingers, a second zone for forming a second electrode with second fingers, and an intermediate zone where the first and the second zones overlap in which the fingers of the first and the second electrodes are to be formed, such that they form interdigitated electrodes, defining at least one isolation region for forming three-dimensional isolation structures adjacent each of the electrode regions, each of said isolation regions being located outside the adjacent electrode region and extending at least on opposite sides of the first zone of the adjacent electrode region, forming isolation structures in each isolation region, these structures being shaped for creating shadow zones in which substantially no material is deposited upon directional deposition of conductive material in a predetermined deposition direction, such that these shadow zones provide electrical isolation between conductive material which is deposited in said first zone and conductive material which is deposited outside said first zone, depositing a conductive material by non-orthogonal directional deposition in the predetermined deposition direction, thereby forming these first and second electrodes and shadow zones.

The shape, dimensions, and location of the three-dimensional isolation structures is chosen such that they create shadow zones at the opposite side of the direction of the beam at a predetermined deposition angle such that electrical isolation between two interdigitated electrodes is obtained by means of a structure outside the region where the electrodes are formed in the same process step. The advantage of this method is that electrical isolation between electrodes of the sensor can be obtained without expensive patterning techniques.

According to an embodiment of the first aspect, forming these isolation structures comprises forming a plurality of interspaced channels and/or hills along opposite sides of at least one of these electrodes. The dimensions and locations of these channels and/or hills is chosen such that shadow zones are created at the opposite side of the direction of the beam, such that the interdigitated electrodes are electrically isolated.

According to another embodiment of the first aspect, forming these isolation structures consist comprises the steps of
forming a plurality of first interspaced channels along opposite sides of the first zone,
forming first hills at the end of these first interspaced channels near the second zone of the electrode region, these hills being sized and located such that each hill creates a shadow zone upon directional depositing the conductive material in which at least one edge of the hill of the subsequent channel is located.

Using this configuration, conductive material between the interspaced channels can be electrically isolated from the conductive material within the electrodes. As a result, coupling between conductive material connecting the fingers of first electrodes and conductive material connecting the fingers of second electrodes is minimized. That way, the changes in electrical characteristics between the electrodes only result from changes in between the electrode fingers.

According to another embodiment of the first aspect, forming this isolation region further comprises the step of limiting the area wherein said conductive material is deposited such that said isolation structures extend beyond said area at least on the side of the first zone. In that case the conductive material connecting the fingers in at least this first zone is limited to a certain area that can be used for contacting this electrode with probes. The size of the contacting area can be tuned by properly defining the area where the conductive material is located in combination with the dimensions of the three-dimensional isolation structures.

The particular shape of the hills in another embodiment reduces the amount of material deposited at the sidewalls of said hills, that way reducing the risk of shorts between the electrode fingers. More specific locations, shapes, numbers, and dimensions for these interspaced channels and/or hills in the isolation region are discussed in the detailed description.

According to embodiments of the first aspect, forming the interdigitated electrodes in the electrode region consists of forming a plurality of interspaced channels and/or hills in the intermediate zone. The dimensions and locations of these channels and/or hills are chosen such that a shadow zone is created at the opposite side of the direction of the beam, such that the fingers of the interdigitated electrodes are electrically isolated. In principle the interdigitated electrodes in the electrode region can be produced by any method known in the art, but the method for forming the isolation structures by a combination of appropriate three-dimensional structures in an insulating substrate and a single and directional deposition of conductive material is especially cost-effective when interdigitated electrodes are also produced by the same method. In that case the patterning of three-dimensional structures for creating the interdigitated electrodes and the patterning for creating the isolation structures can be done in one single step, as well as the directional deposition of the conductive material on both the electrode region and isolation region.

According to embodiments of the first aspect, forming the interdigitated electrodes in the electrode region comprises forming a plurality of interspaced channels having a predetermined depth and width sufficient for maintaining a separation between the conductive material at both sides of these channels upon directional depositing the conductive material, forming hills at alternating ends of these channels, these hills being sized and located such that each hill creates a shadow zone in the deposition direction in which at least the end of the subsequent channel is located such that the interdigitated electrodes are electrically isolated upon directional depositing said conductive material.

The function of the hills is to create electrical isolation at the outer parts of the electrode fingers. The channels provide electrical isolation between the electrode fingers. To optimise the detection efficiency, the spacing between the electrode fingers preferably has dimensions comparable to the dimensions of the molecules to be detected. In this configuration, the spacing between the fingers of the electrodes can be tuned by properly defining the dimensions of the channel in combination with the exact angle of deposition. Furthermore, the number of channels can be chosen such that statistically relevant data are obtained. Also the number of channels defines the area of the region connecting the fingers of the electrode, in which contacting will be done.

More specific locations, shapes, numbers, and dimensions for these interspaced channels and/or hills in the electrode region are discussed in the detailed description.

Specific angles for this directional deposition, location of the conductive material on the substrate and materials are disclosed in different embodiments and are discussed in the detailed description.

According to embodiments of the first aspect, the insulating substrate including three-dimensional structures are polymer replicas formed by moulding using mould inserts. These mould inserts are manufactured by electroplating thereby forming a reverse copy of a master structure. A master structure can be made of silicon using micro-electronics patterning techniques. Possible materials for the insulating substrate are discussed in the detailed description.

In a second aspect, a sensor comprising at least 2 interdigitated electrodes is described. This sensor is produced by non-orthogonal directional deposition of a conductive material on an insulating substrate, so shows the same advantages as have been set out above with respect to the method, and comprises at least one electrode region comprising a first zone in which a first electrode is formed, a second zone in which a second electrode is formed and an intermediate zone where the first and the second zones overlap and in which interdigitated fingers of the first and the second electrodes are located, such that interdigitated electrodes are formed, at least one isolation region adjacent each of the electrode regions, each of said isolation regions being located outside the adjacent electrode region and at least on opposite sides of the first zone of the adjacent electrode region, three-dimensional isolation structures in the insulating substrate in each of these isolation regions, these isolation structures being shaped for creating shadow zones in which substantially no material is deposited upon directional deposition of conductive material in a predetermined deposition direction, shadow zones resulting from being obstructed by these isolation structures during this directional deposition of conductive material, providing electrical isolation between conductive material in the first zone and conductive material outside this first zone.

In an embodiment of the second aspect these three-dimensional isolation structures comprise a plurality of interspaced channels and/or hills located along opposite sides of at least one of these electrodes, these channels and/or hills being located and having predetermined dimensions sufficient for maintaining electrical isolation between the interdigitated electrodes upon directional depositing the conductive material.

In another embodiment of the second aspect these three-dimensional isolation structures comprise a plurality of interspaced channels along opposite sides of the first zone, hills at the end of these channels near said second zone, shadow zones resulting from being obstructed by these hills during directional deposition of conductive material in which at least one edge of the hill of the subsequent channel is located.

In an embodiment of the second aspect, the conductive material is located in a limited area such that said isolation structures extend beyond said area at least on the side of the first zone More specific locations, shapes, numbers, and dimensions for these interspaced channels and/or hills in the isolation region are disclosed in different embodiments. They are discussed in the detailed description.

In an embodiment of the second aspect, the interdigitated electrodes consist of a plurality of interspaced channels and/or hills. On part of these channels and/or hills a conductive layer is located such that the two electrodes of the interdigitated electrode are electrically isolated The dimensions and locations of these channels and/or hills are chosen such that a shadow zone is created at the opposite side of the direction where the beam comes from, such that electrical isolation between the two electrodes of the interdigitated electrode is obtained.

According to embodiments of the second aspect the electrode region comprises a plurality of second interspaced channels and/or hills in the intermediate zone being located and having dimensions sufficient for maintaining electrical isolation between the fingers of the interdigitated electrodes upon directional depositing the conductive material.

According to embodiments of the second aspect the electrode region comprises
  a plurality of interspaced channels having a predetermined depth and width sufficient for maintaining a separation between the conductive material at both sides of the channels upon directional depositing the conductive material,
  second hills at alternating ends of these second channels,
  shadow zones resulting from being obstructed by these hills during directional deposition of conductive material, each shadow zone encompassing at least the end of the subsequent channel for electrically isolating these interdigitated electrodes from each other.

More specific locations, shapes, numbers, and dimensions for these interspaced channels and/or hills in the electrode region are disclosed in different embodiments. They are discussed in the detailed description.

According to embodiments of the second aspect, the insulating substrate including three-dimensional structures is made of a polymer material. Possible materials for the insulating substrate are disclosed.

In a third aspect, an interdigitated electrode array is described comprising a plurality of electrode regions, having first electrodes electrically isolated from each other by isolation structures and at least part of the second electrodes electrically connected.

In an embodiment of the third aspect, these electrodes are arranged in a geometric array of a predefined number of rows and columns. These columns are electrically isolated from each other by regions where no conductive material is deposited. The isolation regions extend alongside the first electrodes into these regions without conductive material, thereby electrically isolating the first electrodes within each column and electrically connecting the second electrodes of each column.

In a fourth aspect a sensor apparatus is described comprising
  at least one sensor according to any of the embodiments of the second and the third aspect,
  means for contacting each of the first and second electrodes,
  means for applying a voltage on each of the first and second electrodes,
  means for measuring the electrical properties or the impedance between the first and second electrodes of the same electrode region,
  means for applying a sample solution to be tested onto these sensors.

Optionally probes for binding to molecules, present in a sample to be tested, can be immobilized onto the individual sensors. These probes can be applied to either the insulating part of the channels and/or to the surface of the electrodes.

Particular and preferred aspects of the invention can be found in the independent and dependent claims. Features from the dependent claims may be combined with features of the independent claims and with features of other dependent claims.

The characteristics, features, and advantages of the invention will be clarified in the detailed description in combination with the drawings, which illustrate the principles of the invention. This description is given as an example only, without limiting the scope of the invention.

DETAILED DESCRIPTION AND PREFERRED EMBODIMENTS

Figure 1:
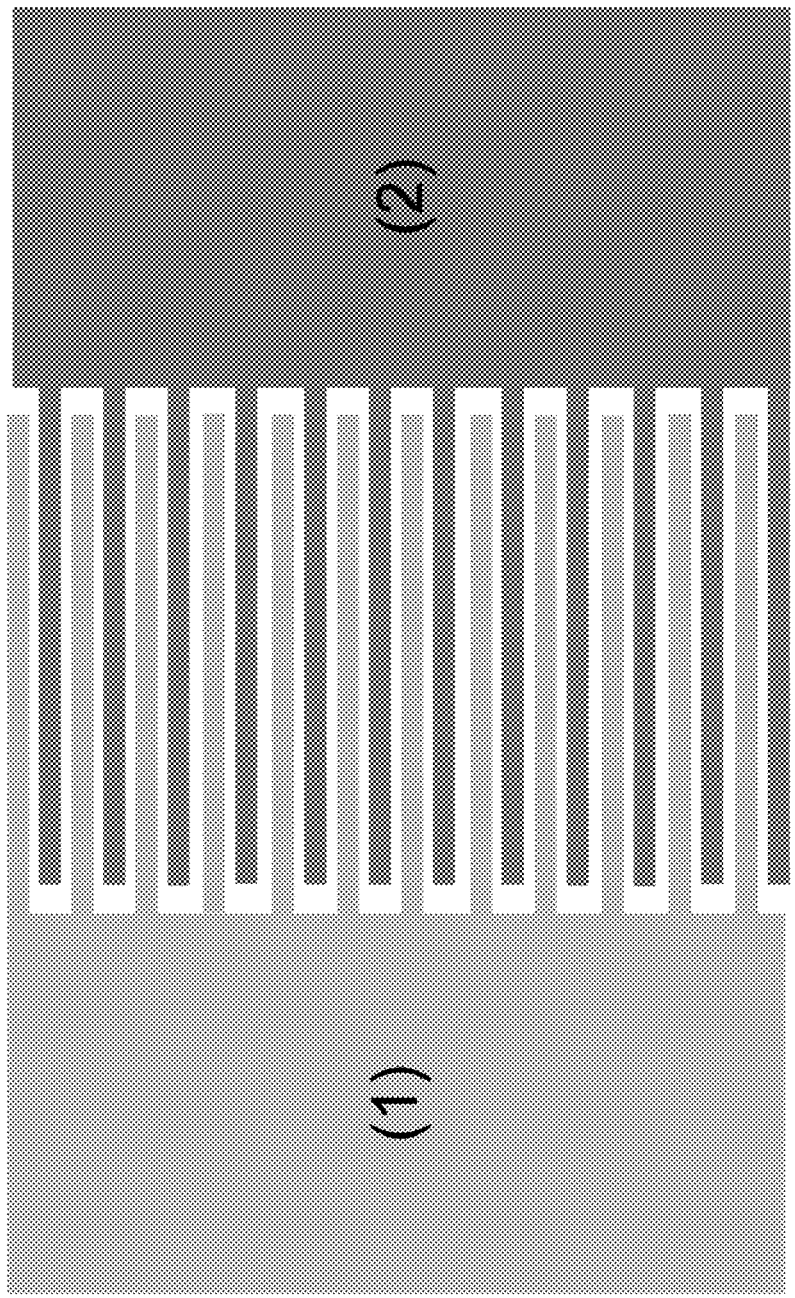
FIG. 1 illustrates the shape and location of interdigitated electrodes, comprising electrode 1 (1) and electrode 2 (2).

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and that the embodiments of the invention described herein can operate in other orientations than described or illustrated herein.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B.

In the first aspect, a method to produce a sensor comprising interdigitated electrodes is described. The method is based on a combination of appropriate three-dimensional structures in an insulating substrate and a single and directional deposition of conductive material. In order to ensure sufficient electrical isolation and individual, but convenient, accessibility of the sensors in the array, the interdigitated electrode regions need to be complemented with specific features on the three-dimensional structures. Combined with the use of e.g. shadow masks in the deposition step, these features allow for the site-specific deposition of the conductive material. The technology described has the additional advantage to integrate highly miniaturized and arrayed electronics elements into polymer micro-fluidics technology, which leads to the affordable manufacturing of (bio)sensor arrays.

In the second aspect, a sensor comprising interdigitated electrodes is described. The sensor comprises an insulating layer with conductive interdigitated electrodes on the top. The insulating substrate comprises three-dimensional structures. These interdigitated electrodes comprise 2 electrodes having a plurality of fingers. The fingers of the two electrodes are arranged in an interdigitated way, as illustrated in FIG. 1. The region where these electrodes are located is called "electrode region". The conductive layers are arranged in a specific geometry thereby enhancing the detection sensitivity of the sensor.

As the sensor and the method to produce the sensor are closely linked, both aspects will be considered together in the description below.

For detecting the presence or absence of molecules, interdigitated electrodes are formed on an insulating substrate. They comprise two electrodes (see FIG. 1) called first electrode (1) and second electrode (2). In principle these interdigitated electrodes can be created by any method known in the art. A conductive layer can be deposited on an insulating substrate, followed by lithography and wet and/or dry etching. For patterning interdigitated electrodes lift-off techniques can be used.

These interdigitated electrodes are preferably produced along with the isolation by a method based on a combination of appropriate three-dimensional structures in an insulating substrate and a single, directional deposition of conductive material. In order to ensure sufficient electrical isolation and individual, but convenient, accessibility of the sensors in the array, the interdigitated electrode regions need to be complemented with specific features on the three-dimensional structure. Combined with a method to limit the conductive material to a limited region, these features allow for the site-specific location of the conductive material. In an embodiment, these three-dimensional structures consist of a plurality of interspaced channels and/or hills. These channels and/or hills are located and have dimensions such that the shadow zones, created by directional deposition of the conductive material, result in electrical isolation between both electrodes.

Figure 2:
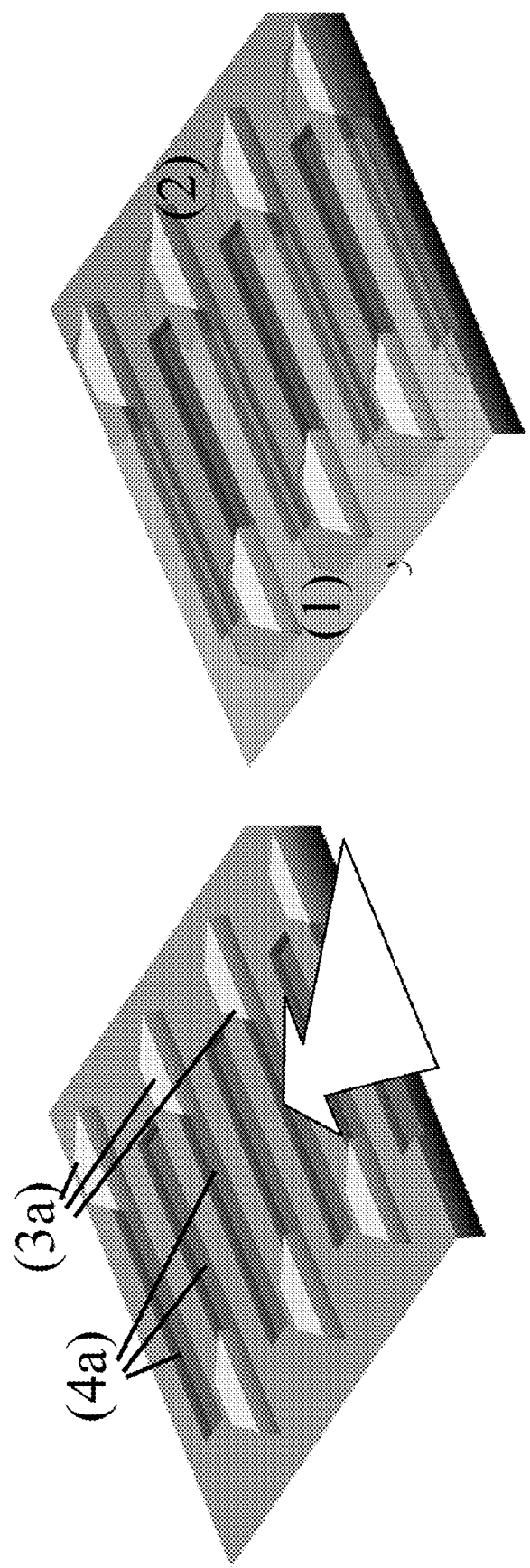
FIG. 2 shows a method to prepare interdigitated electrodes based on a combination of hills and channels in an insulating substrate in combination with directional deposition of a conductive material. In the drawing on the left, hills (3) and channels (4) in the insulating substrate are shown prior to depositing the conductive material. Arrows in the figures indicate the deposition direction. On the right, the shadow zones created by hills and channels upon directional deposition of the conductive material can be observed, thereby creating interdigitated electrodes. The two electrodes (1) and (2) are indicated in different grey scales.
Figure 3:
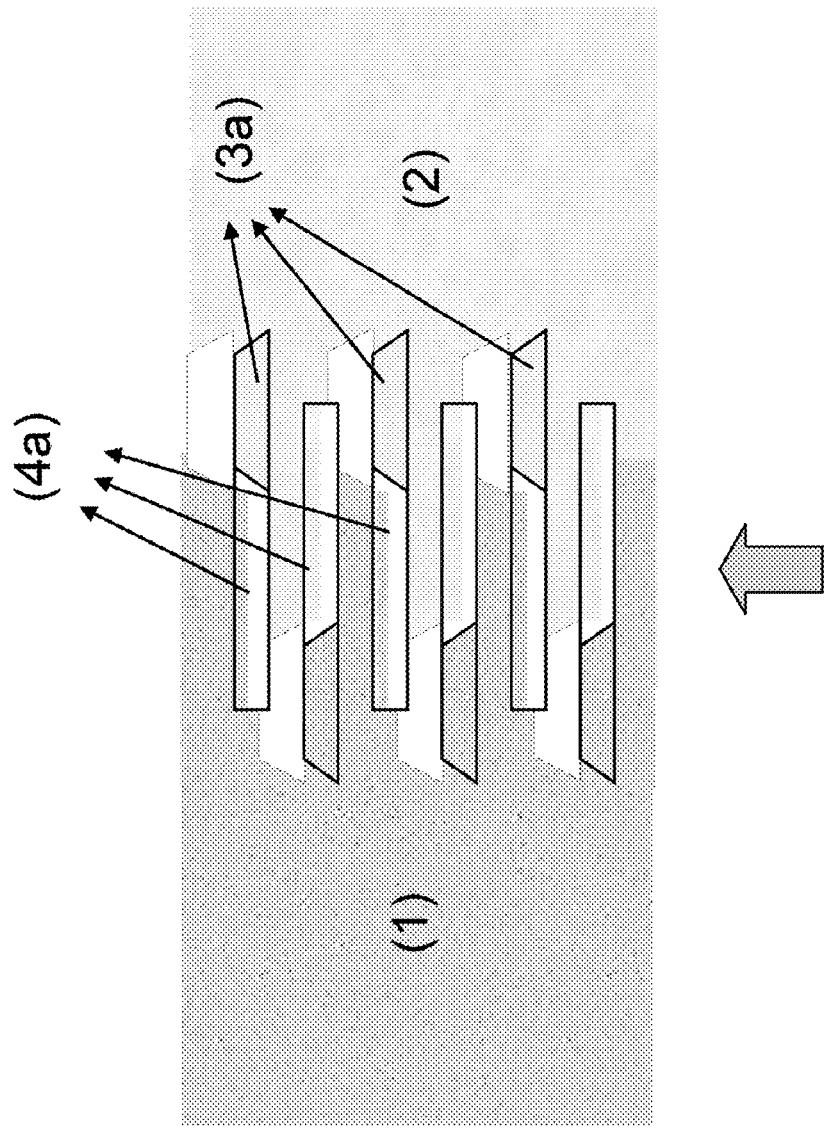
FIG. 3 shows a topview picture of interdigitated electrodes prepared according to the method illustrated in FIG. 2.

In another embodiment, a plurality of interspaced channels and/or hills is created in the insulating substrate. The base structure is shown in FIG. 2, at the left side. The structure shows 2 functional elements: channels (3a) and hills (4a). The channels are below the base plane and the hills are elevated above the base plane. The interdigitated electrodes (1) and (2) are realized with a directional deposition process of a conductive material. The direction in which this conductive material is deposited is indicated with an arrow in FIG. 2. Interspaced channels are created within the sensor area in the insulating substrate having essentially the same direction. The backside, from a viewpoint of the evaporation direction, of the channels as well as part of the bottom of the channels is shadowed from the evaporated material (see FIG. 2, right). The channels provide a separation between the adjacent electrode fingers. That way, the channels provide electrical isolation between the interdigitated fingers. The exact area of the bottom of the channel that is shadowed from the evaporated material depends on the exact angle of deposition. The channels have dimensions such that conductive material at opposite sides of the channels is electrically isolated. Hills are formed at alternating ends of these channels (FIG. 2, left). The function of the hills is to create electrical isolation at the outer parts of the electrode fingers. At the backside of the hills, from a viewpoint of the evaporation direction, a shadow zone is created shadowing part of the base plane in between two channels and the end of the subsequent channel (FIG. 2, right), thereby electrically isolating the end of the fingers of each of the first electrode from the second electrode. In FIG. 3 a topview picture of this embodiment is shown. In the remaining of the detailed description, mainly topview pictures will be used to illustrate different embodiments. In these pictures, the direction in which this conductive material is deposited is indicated with an arrow. Electrode 1 is indicated with (1), electrode 2 with (2), hills with (3a), and channels with (4a).

In another embodiment, the number of channels in the electrode region is at least more than 4, or even better more than 10, or in between 10 and 100, or in between 10 and 500, preferably between 50 and 500, possibly more than 500. The number of channels is chosen such that statistically relevant data are obtained. This means that enough binding should occur in the electrode region. Furthermore contacting the electrode is done in the region connecting the fingers of both electrodes. This region needs to be large enough to allow contacting the regions with external probes. Enlarging the area can be achieved by increasing the number of fingers of the electrodes.

The width of the electrode fingers and the spacing between the fingers of different electrodes are chosen depending on the dimensions of the molecular structure to be detected. The spacing between the fingers of the interdigitated electrodes is chosen comparable to the dimensions of the molecular structure that needs to be detected. The distance between the fingers of the interdigitated electrodes depends on the width and depth of the channels and the angle at which the conductive material is deposited. This means that the width and depth of the channels is chosen depending on the molecular structure that needs to be detected, in combination with the deposition angle of the conductive material.

In another embodiment, the interspaced channels both in the electrode region and at the edges of the electrode region have a height and a width in the same order of magnitude. The height and the width may be exactly the same for all channels or may vary from one channel to the other. The height and the width are preferably chosen between 10 nm and 10 µm, or between 250 nm and 5 µm, preferably between 1 µm and 5 µm.

As can be observed in FIGS. 2 and 3, the conductive material needs to be electrically isolated from conductive material surrounding the electrode region. More particular, the conductive material of the top finger and of the bottom finger of the interdigitated electrodes needs to be isolated from surrounding conductive material in order to avoid electrical contact between the two electrodes. Furthermore the size of the conductive area connecting the fingers of the individual electrodes needs to allow contacting the electrodes. The area near the sensor region where the isolation is created is called "isolation region".

Limiting the material may be done by any method known in the art. The conductive material may be deposited through a shadow mask. This is indeed a good method to limit the conductive material connecting the fingers, as this is referred to as a large area. In an embodiment, a shadow mask is used for locally depositing said conductive material on the patterned substrate.

Figure 4:
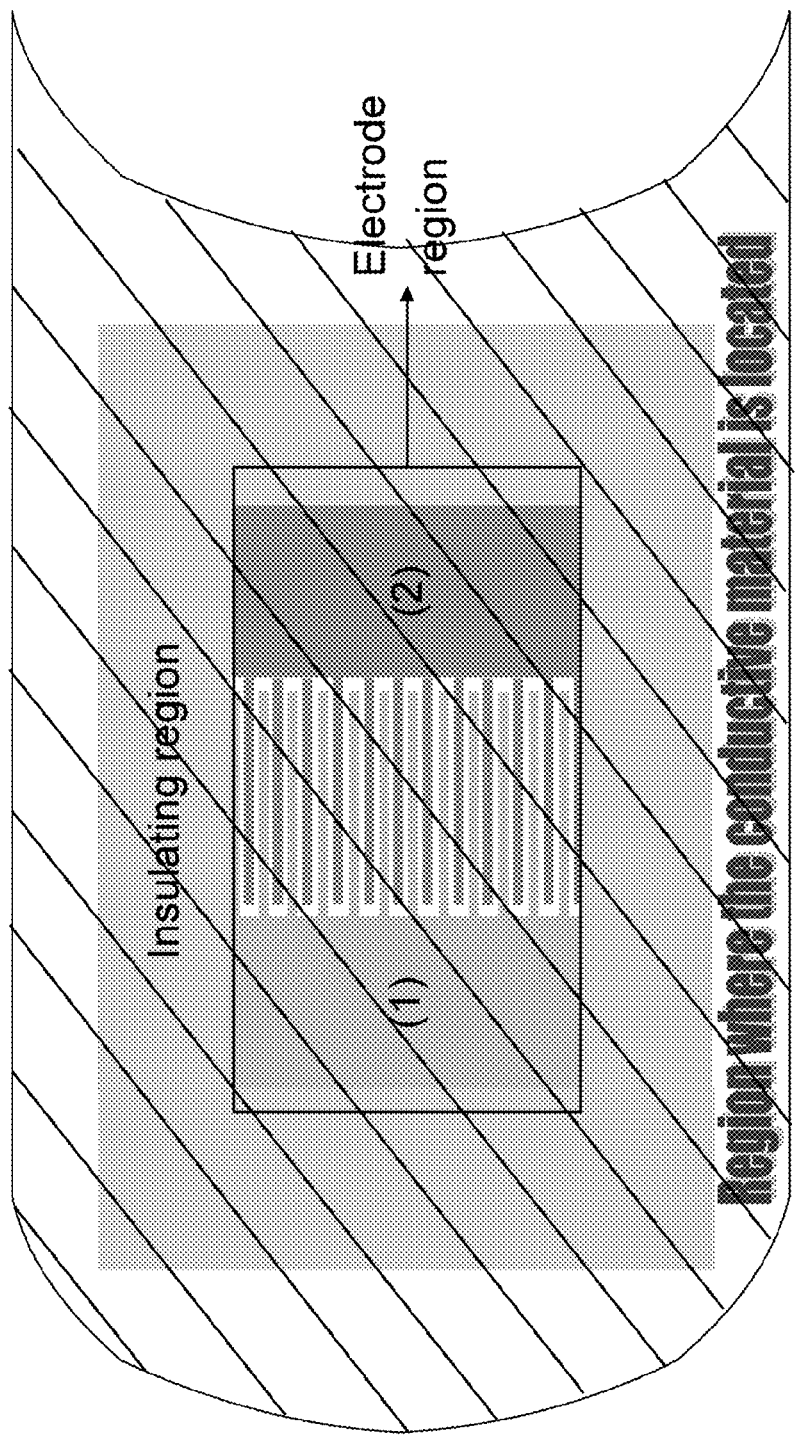
In FIG. 4, a schematic representation is given of a sensor comprising interdigitated electrodes surrounded by a region for contacting and isolating the electrodes.

As the width of the fingers is in the micron or submicron regime, it is very challenging or almost impossible task to align the shadow mask towards those fingers. An alternative is to use microelectronics patterning techniques, which has the disadvantage that many extra processing steps are required, increasing the production cost tremendously. To isolate the material of the top and bottom fingers of the interdigitated electrodes from the surrounding material, a method is developed based on a combination of appropriate three-dimensional structures in the insulating substrate located near the electrode region, at least partially outside the electrode region, within the isolation region (see FIG. 4) and a single and directional deposition of conductive material. After creating three-dimensional structures a conductive material is deposited in a non-orthogonal direction onto the substrate. The angle of deposition is chosen such that these three-dimensional structures create a shadow zone at the opposite side of the direction of the beam thereby creating electrical isolation between these interdigitated electrodes. The method is especially cost-effective when interdigitated electrodes are made by the method described above using a combination of an appropriate three-dimensional structure in the same insulating substrate and a single and directional deposition of conductive material. In that case the patterning of three-dimensional structures for creating the interdigitated electrodes and the patterning for creating three-dimensional structures for electrically isolating the conductive material within a certain region from other regions can be done in one single step. Furthermore, the directional deposition of the conductive material can be done in one step, both in the electrode region and in the isolation region thereby limiting the conductive material to certain well-defined areas.

Figure 5:
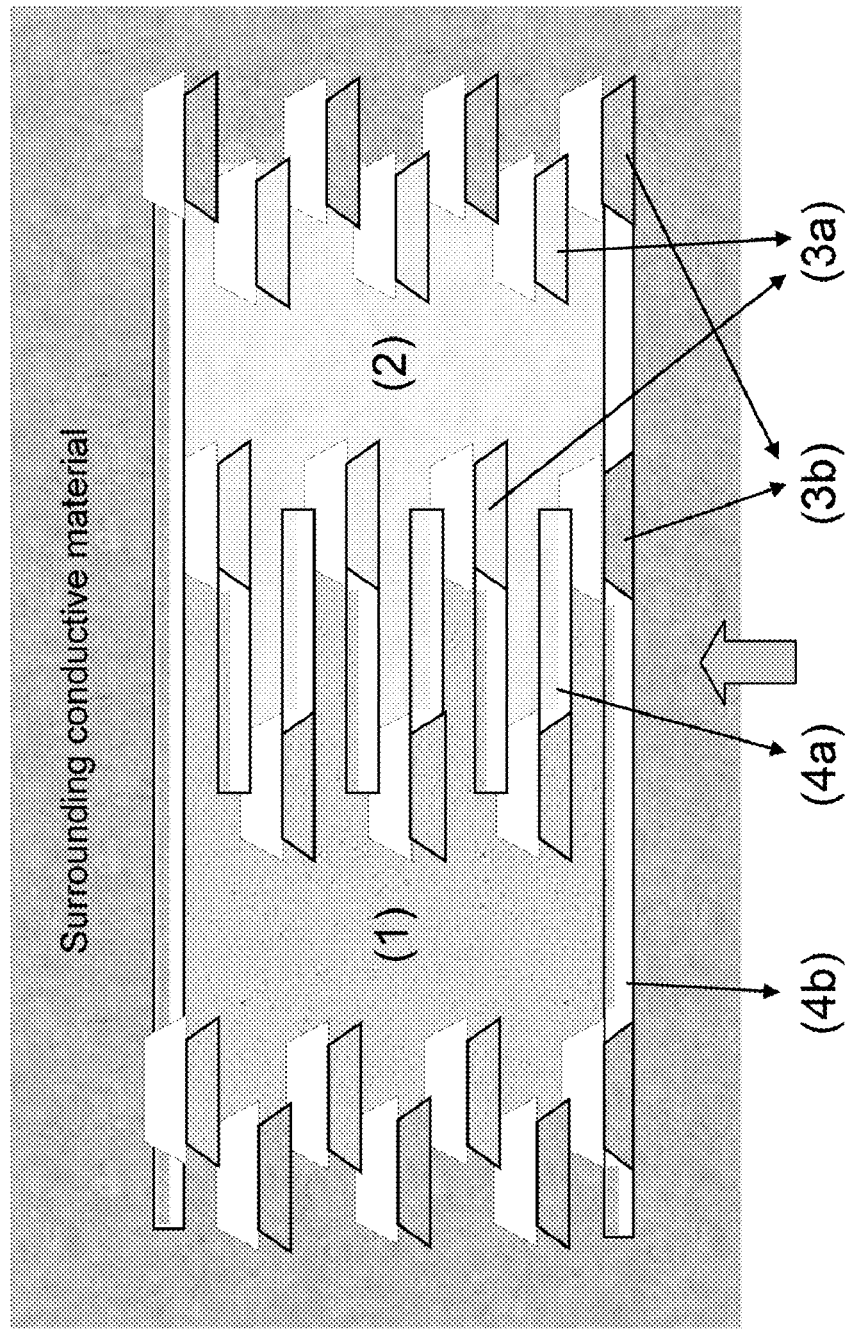
In FIG. 5, a location of channels and hills in the isolation area is illustrated, thereby creating two interdigitated electrodes being isolated from each other and from the surrounding conductive material.

In another embodiment, these three-dimensional structures in the insulation region are composed of a plurality of interspaced channels and/or hills. This can be only channels, only hills, or a combination of channels and hills. These channels and/or hills can be parallel to each other or not parallel to each other. All hills can have different dimensions or the same dimensions, i.e. width, length, and height in case of hills. All channels can have different dimensions or the same dimensions, i.e. width, length, and depth for channels. The dimensions and locations of these channels and hills are chosen such that a shadow zone is created at the backside of the hills or in the channels, where essentially no material is deposited, such that the electrodes are electrically isolated. An example with a possible location of hills (3b) and channels (4b) can be found in FIG. 5.

Figure 6:
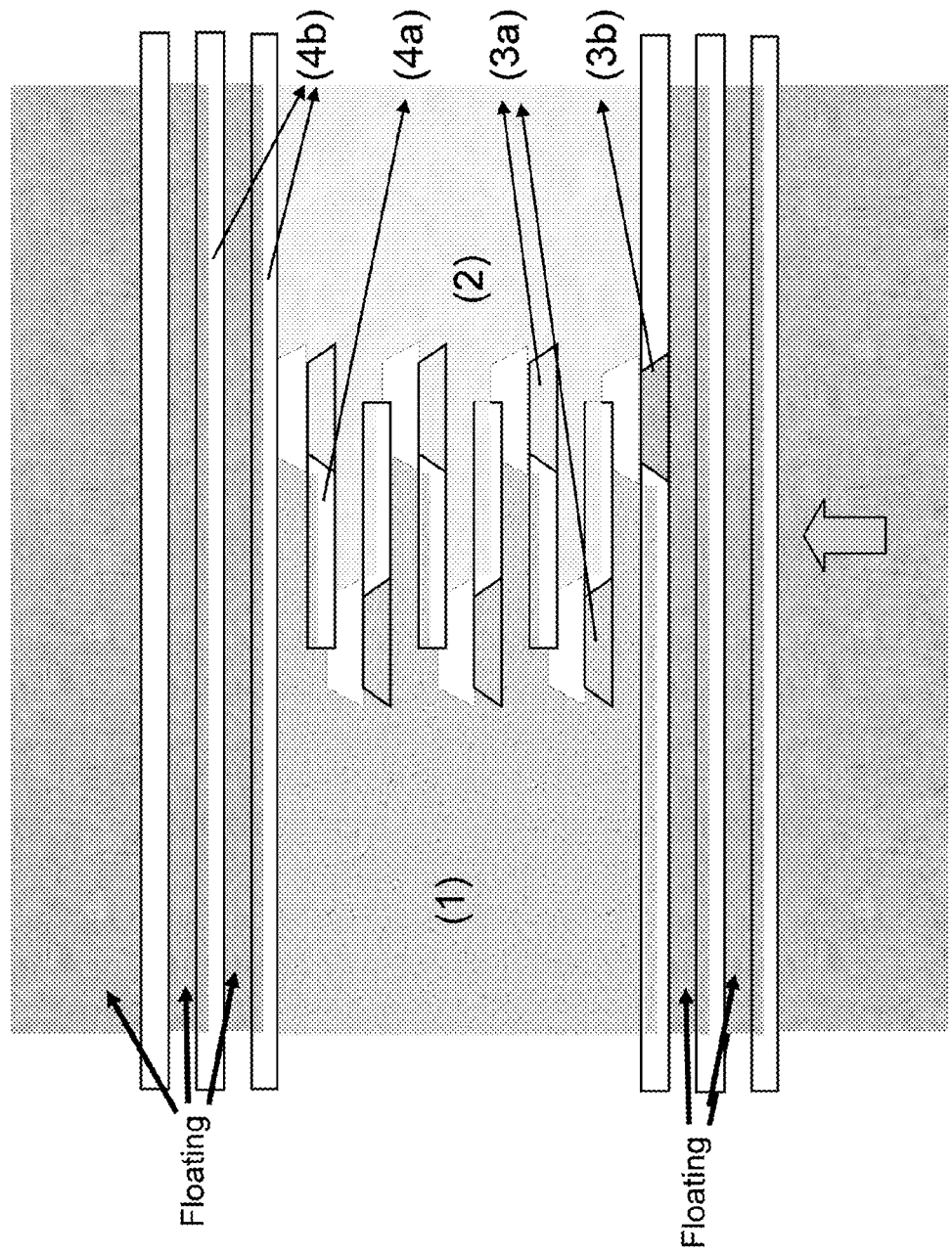
In FIG. 6, a location of channels in the isolation area is illustrated, whereby some channels hills are extending the electrode region, thereby creating two interdigitated electrodes being isolated from each other and from the surrounding conductive material.
Figure 7:
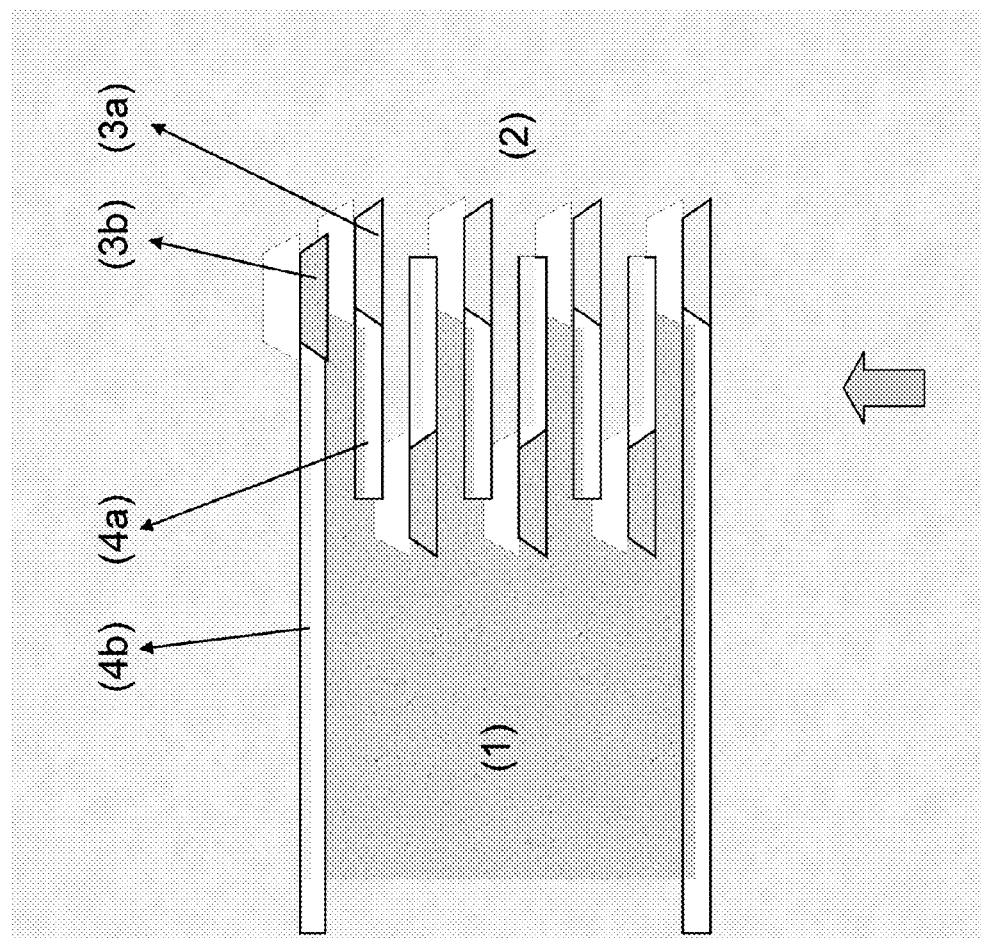
In FIG. 7, a location of channels and hills creating interdigitated electrodes electrically isolated from each other is illustrated. Channels of the insulating region extend between the electrode region at electrode 1 and the region adjacent to electrode 1 where the conductive material is located.
Figure 8:
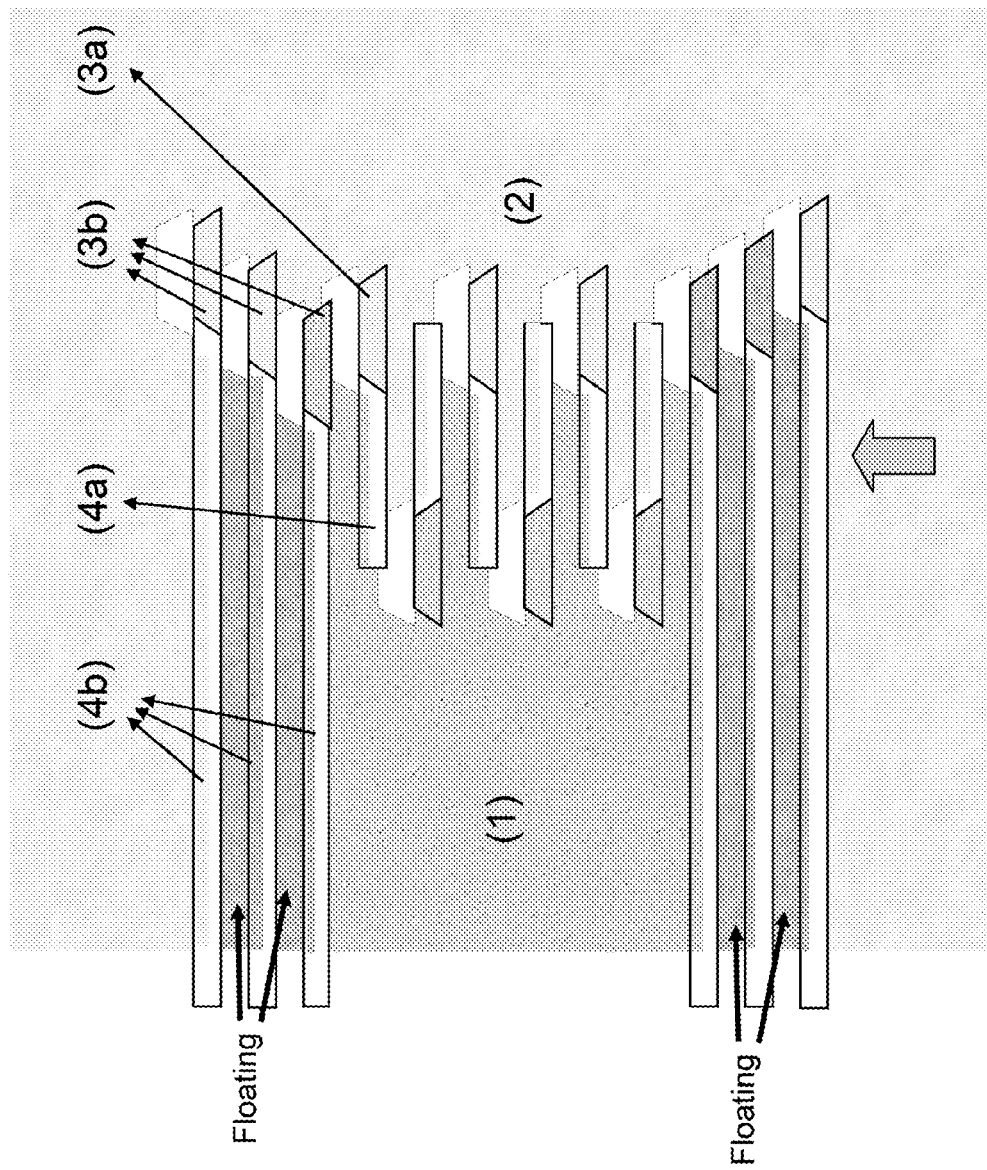
In FIG. 8, another location of channels and hills creating interdigitated electrodes, electrically isolated from each other, is illustrated. Channels of the insulating region extend between the electrode region at electrode 1 and are extending the region adjacent to electrode 1 where the conductive material is located.
Figure 9:
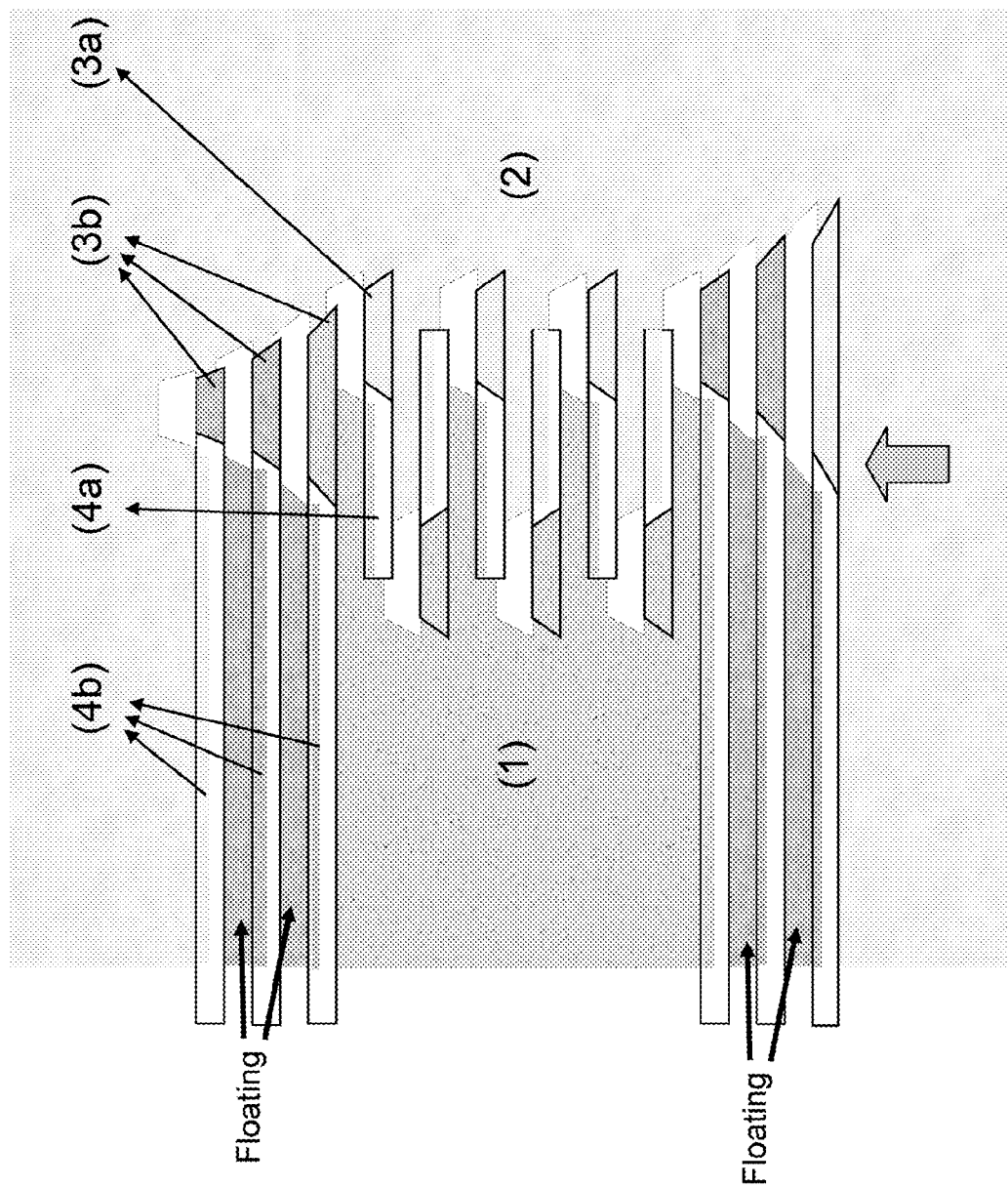
In FIG. 9, another location of channels and hills creating interdigitated electrodes electrically isolated from each other. Channels of the insulating region extend between the electrode region at electrode 1 and are extending the region adjacent to electrode 1 where the conductive material is located.
Figure 10:
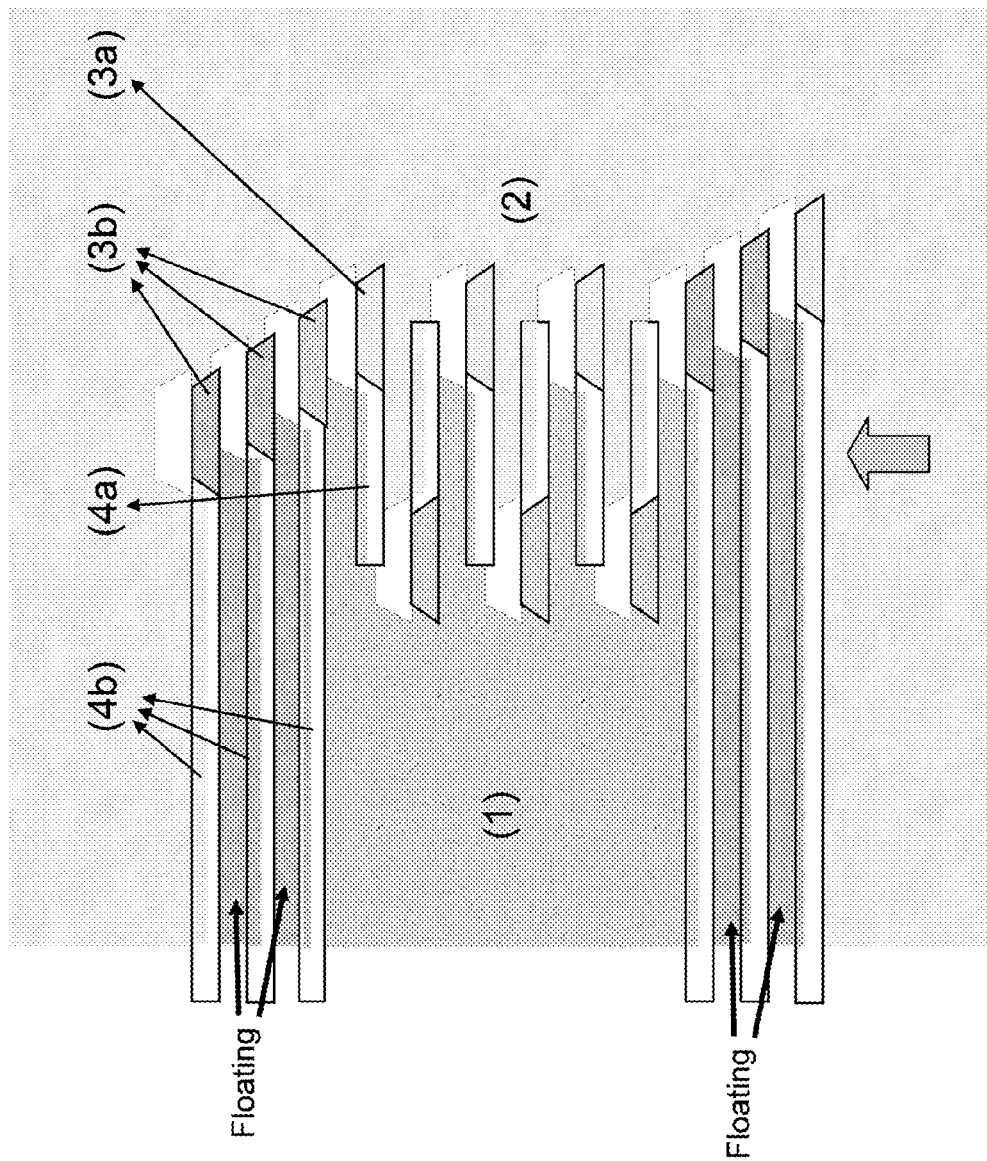
In FIG. 10, the location of channels and hills in a preferred embodiment is illustrated, thereby creating interdigitated electrodes electrically isolated from each other. Channels of the insulating region extend between the electrode region 1 and the region adjacent to electrode 1 where the conductive material is located.

In another embodiment, the conductive material covers only part of the substrate, including the electrode region. Limiting the conductive material to a limited region on the insulating substrate can be done by any method known in the art. This can be achieved by locally depositing said conductive material, for example by using a shadow mask. Another possibility is that the conductive material is deposited on the complete substrate surface and removed for example by micro-electronics patterning techniques, lithography, lift-off, dry etch, wet etch, or their combination, or any other method known in the art to locally remove the conductive material. The three-dimensional structures in the isolation region consisting of channels and/or hills at opposite sides of at least one electrode are extending beyond the region wherein the conductive material is located, thereby creating electrically isolated electrodes. An example of locations of hills (3b) and channels (4b) can be found in FIG. 6.

In another embodiment, the hills and channels composing the three-dimensional structures in the isolation region are located at opposite sides of at least one of said electrodes. At one edge the channels are extending outside the region where conductive material is located; the other edge is located near the electrode region. At this edge near the electrode region, hills are located, thereby creating electrodes electrically isolated from each other. Examples of possible arrangements of channels (4b) and hills (3b) can be found in FIGS. 7, 8, 9, and 10. The hills can have the same width as the corresponding channels or they can have a different width.

In case of a plurality of channels, the width, length, and height of the hills is chosen such that the shadow zone created at the back side of the hill during directional deposition covers at least one edge of the subsequent channel and part of the top of the hill of the subsequent channel. The subsequent channel is the channel at the backside of said channel when looking from direction of the beam. That way the material in between those channels is floating. The advantage is that the conductive material connecting the fingers of the first electrode is separated from the conductive material connecting the fingers of the second electrode by this plurality of interspaced channels. That way a physical distance between these materials is increased such that coupling between the materials connecting the fingers is minimized and the impedance measured between the electrodes is mainly influenced by a change in the impedance between the electrode fingers. In an embodiment, the number of channels located in the isolation region is at least more than 2, or more than 10, or in between 10 and 100, or in between 10 and 500, preferably between 100 and 500, or more than 500. The choice of the number of the channels is important in case the conductive material in between the channels is floating in order to minimize coupling between the materials connecting the fingers of the electrodes. Furthermore, increasing the area where the conductive material is located, in combination with longer channels, increases the area connecting the electrode fingers, making contacting with probes easier.

In another embodiment, the hills in the isolation region are created such that the edges are tapered (see FIGS. 8, 9, and 10): that way each hill creates a shadow zone at the backside of the hill during directional deposition covering the tapered edge of the hill of the subsequent channel. The subsequent channel or hill is the channel or hill at the backside of said channel when looking from the direction of the beam. In this context tapered edges means that the same edge, always left or always right, of the subsequent hill is located behind the previous hill when looking from the direction of the beam.

Figure 11:
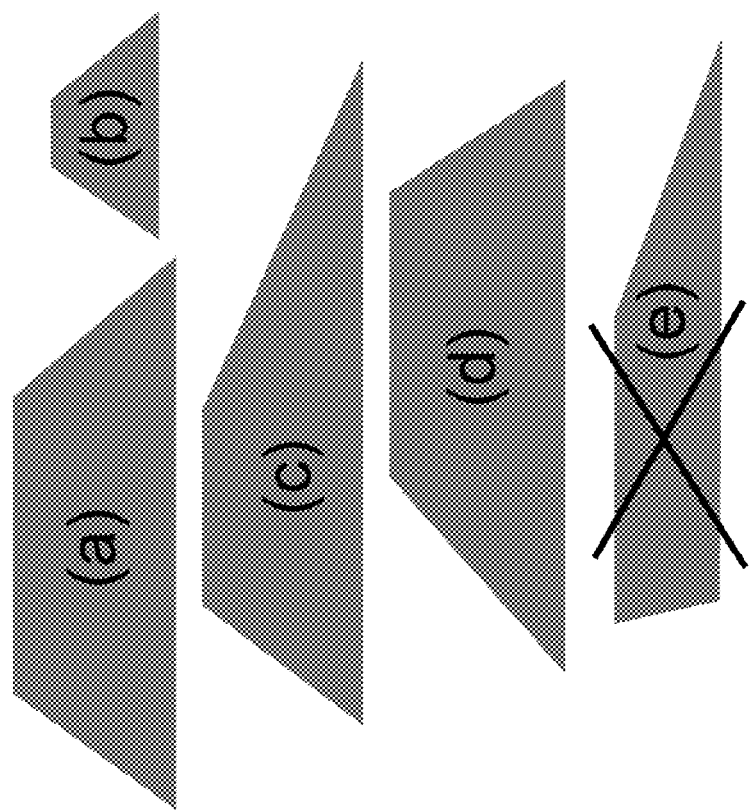
FIG. 11 illustrates possible trapezoidal shapes for the hills. Two edges (top and bottom edges in the figures) are parallel, one of these edges is shorter than the other edge. The longest edge always exceeds the shortest edge at two sides, meaning that shape (e) is unsuitable.

In principle the top surface of the hills may have any shape. At least one edge of the hill needs to be free of conductive material to avoid electrical contact between the conductive materials of the different electrodes. In an embodiment, the hills are made with a top surface having a trapezoidal shape. A trapezoid is a 2-dimensional surface having 2 parallel sides of different length. The lines connecting those parallel edges make an angle below 90° with the longest of these parallel sides and an angle larger than 90° with the shortest of these parallel sides. The parallel sides are parallel to the direction of the channels, whereby the shortest of these parallel sides is located at the backside when looking from the direction of the beam. Examples of trapezoidal shape are represented in FIG. 11.

In principle any conductive material can be used for the directional deposition. Frequently used materials, presented in an embodiment, are Au, Ag, Pt, Pd, Cu, Al, Ta, Ti, and Indium Tin oxide (ITO). The conductive layer can be a thin film. At least all material within one electrode needs to be connected to each other. In the best case, the conductive layer is a uniform continuous thin film. The thickness of the film is at least 5 nm, even better between 25 nm and 500 nm, preferably between 100 nm and 250 nm.

In another embodiment, deposition methods are represented for depositing said conductive layer, i.e. physical vapour deposition (PVD), self-ionised plasma (SIP) deposition, e-beam evaporation, and thermal evaporation.

In another embodiment, angles for the directional deposition are selected. As the directional deposition is non-orthogonal, the angle is below 90° with respect to the normal to the substrate, better between 30° and 89°, preferably between 60° and 85° with respect to the normal on the insulating substrate. The angle is chosen such that the shadowing effect of the hills and the channels creates electrical isolation between the interdigitated electrodes. Furthermore, this angle is chosen such that the distance between the fingers of the electrodes matches with the envisaged molecules.

On top of these three-dimensional structures defining the electrode regions and insulating regions, the insulating substrate can comprise three-dimensional registering features, such as positioning cones or grooves, which can be used for physical referencing in subsequent processing steps.

The three-dimensional structures in the insulating substrate can be made by any method known in the art. It can be made by microelectronics patterning techniques, using known lithography techniques, e.g. photolithography, preferably UV lithography, even more preferably deep UV lithography, followed by a selective etching. In that case all process steps need to be repeated for every single substrate.

Therefore, cost-effective methods to prepare the insulating substrate are represented in several embodiments. The insulating substrate including the three-dimensional structures can be replicas formed by (injection) moulding, using negative mould inserts or any other method, know in the art, to make replicas. The mould inserts can be re-used as a tool for further replication processes. After hardening in the mould inserts, the mould materials have reached a sufficient strength and the separation of mould and mould insert can take place. For the realization of micro-moulding and micro-reaction injection moulding the extremely low roughness of the walls of the mould inserts is most important. Such mould inserts can be made with LIGA using X-ray or photolithography, preferably UV lithography, more preferably deep UV lithography, which allows one to achieve very small dimensions. The mould inserts can also be manufactured by electroplating as a reverse copy of a master structure. The mould inserts can be made out of nickel. In an embodiment, the master structure is made of a silicon master structure using microelectronics patterning techniques. In more detail the following steps can be used. Channels are patterned with a resist layer and dry-etched in bare silicon. A stack of materials for forming the hills is deposited. Any material having a planarizing effect can be used. Chemical mechanical polishing is used to further planarize this stack to allow high-resolution lithography for patterning the hills. Finally the hills are dry-etched into this stack. This results in a positive copy of the insulating substrate.

This insulating substrate can be made out of an insulating material or can be any material having an insulating top surface. An insulating layer formed on the substrate can be a polymer layer such as polyimide or BCB, can be a dielectric or insulating layer such as $Si_3N_4$ being deposited by LPCVD or PECVD techniques or $SiO_2$ deposited or thermally grown on another material. An insulating substrate including the three-dimensional structures can be made of a crystalline material such as quartz or silicon, or an amorphous material such as a glass wafer, or a thick film substrate, such as $Al_2O_3$ or can be a polymer. Cheap plastic base materials can be produced by injection moulding or hot embossing once a negative master is produced. In case of micro-moulding, materials used for micro-replication include low viscosity thermoplastic polymers like polymethyl methacrylate (PMMA), polysulfon (PSU), polybutylene terephthalate (PBT), cyclo olefin copolymer (COC), polyoxymethylene (POM), polyphenylene (PPS), polyamide (PA), or polycarbonate (PC), as well as reaction resins based on methacrylates, silicones and caprolactames. Except for filled moulding materials, almost any material suitable for macroscopic moulding can be used for micro-moulding. Many more materials can be used.

In other embodiments, said sensor comprises probes for binding to molecules present in a sample to be tested. These probes can be applied to either the insulating part of the channels and/or to the surface of the electrodes. These probes can be peptides, enzymes, antigens, antibodies, oligonucleotides, DNA or RNA fragments, said probes being covalently or non-covalently attached to said sensor. Also indifferent probes or non-specific conditioning molecules can be applied to either the insulating part of the channels and/or to the surface of electrodes in such a way that this structure effectively acts as a reference structure for back-ground monitoring.

As temperature tracking element, at least one of the electrodes can be provided with a material of known temperature behaviour for monitoring the temperature behaviour during operation.

In the third aspect, an interdigitated electrode array is presented. It comprises a plurality of electrode regions, electrically isolated from each other by isolation structures as described in the second aspect. The first electrodes of each sensor are electrically isolated and at least part of the second electrodes is electrically connected.

Figure 12:
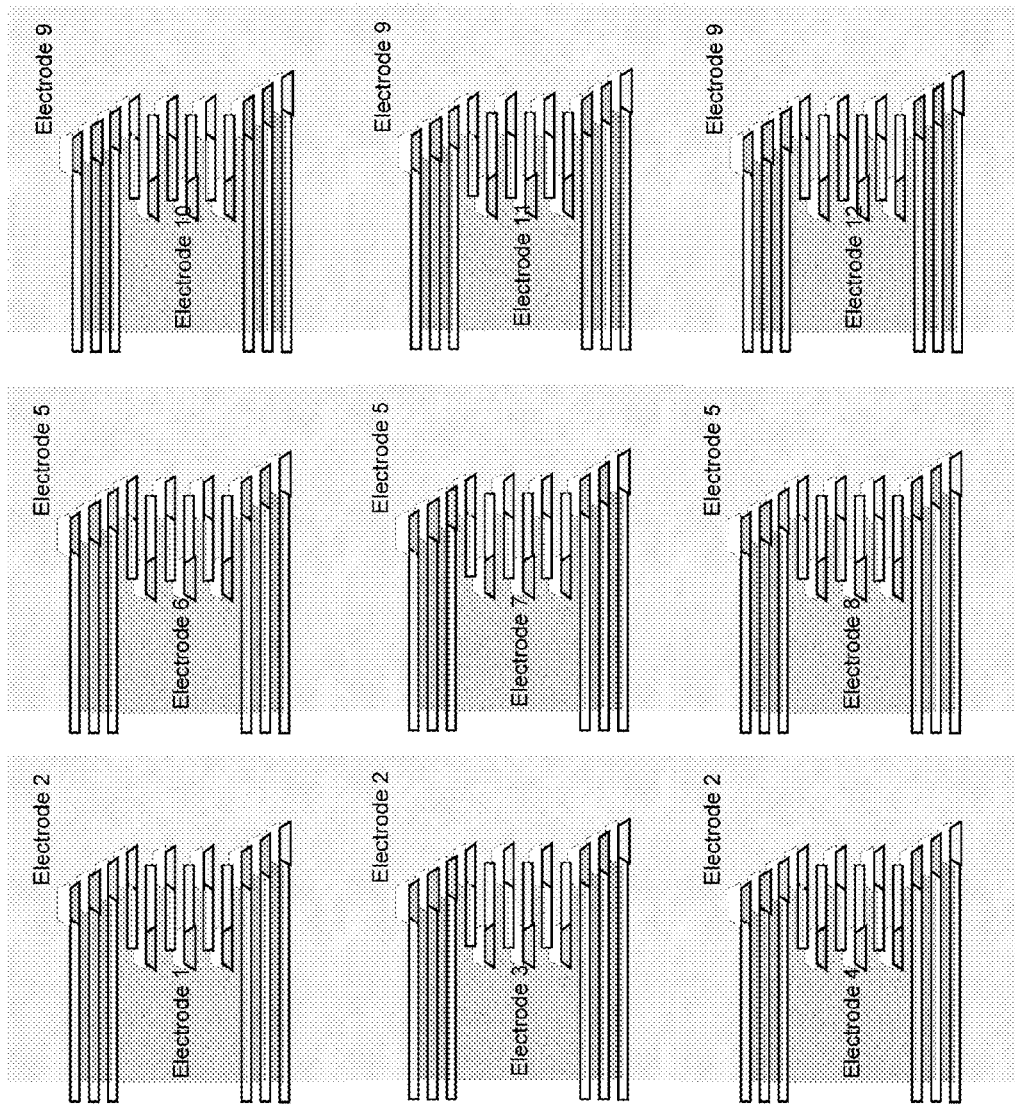
FIG. 12 shows an array of interdigitated electrodes. By electrically connecting one of the electrodes of the interdigitated electrodes of all sensors in a column, the number of contacts to the array can be reduced.

In a preferred embodiment, the individual sensors are arranged in a geometric array in a number of rows and columns. The arrangement of the electrodes in this specific array is represented in FIG. 12. The direction of the channels in the individual sensors is essentially parallel to each other. The channels are parallel to the rows of these sensors. The conductive material is located in columns covering the electrode regions of the sensors of that row. At one side the conductive material extends the electrode region and the isolation region, thereby electrically connecting one electrode of each sensor in that column. At the other side the channels of the isolation region extend the region where the conductive material is located. That way the first electrode of each sensor is electrically isolated from the other electrodes. The advantage is that the impedance of the individual sensors can be measured with a limited number of contacts. In the standard approach, the number of contacts equals two times the number of sensors, as each sensor comprises two electrodes. In this case, one of the electrodes of each sensor in a column is connected. Only one connection is needed to contact this one electrode in all sensors on a column. The other electrode of each sensor needs to be connected separately. This results in a total number of contacts=number of sensors+number of columns.

In the above embodiment the channels have a width of 1 µm and spacing of 1 µm. As there are 125 channels in the electrode region, the width of the isolated electrode, which is the width of the contacting area, is 250 µm. The length of the channels is 1500 µm, the length of the contacting area of the isolated electrode is in between 500 and 1250 µm, depending on the accuracy with which the shadow mask can be positioned. Also in the isolation region, there are 125 channels, such that the distance between the materials of the two electrodes connecting the fingers is 250 µm, thereby limiting the electrical coupling between the two electrodes connecting the fingers. That way changes in impedance between the interdigitated electrodes are only caused by changes in impedance between the fingers of the electrodes.

Figure 13:
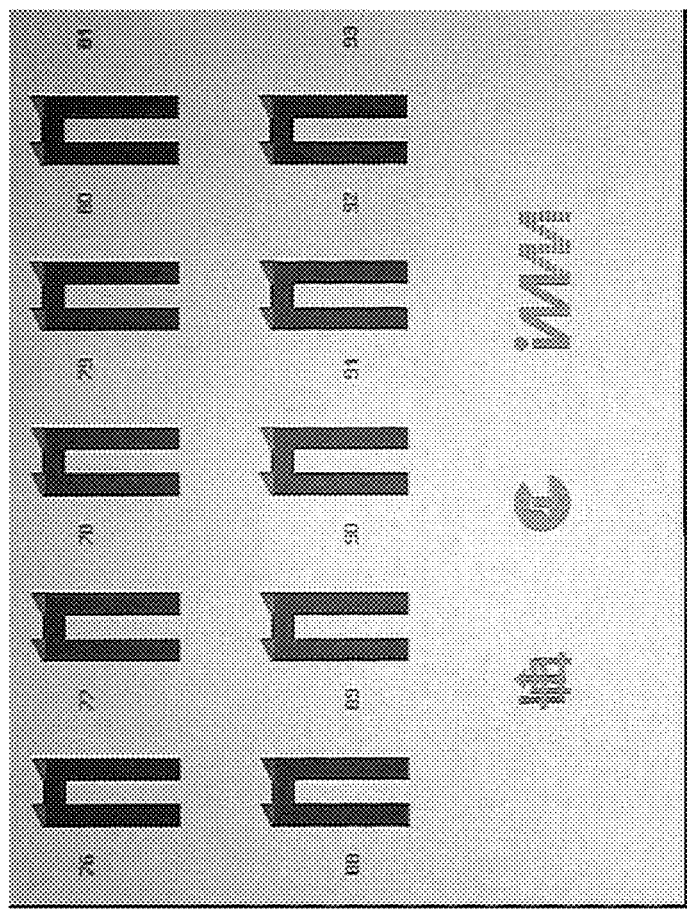
FIG. 13 shows a picture taken with an optical microscope of the three-dimensional structures of 10 interdigitated electrodes arranged in an array according to the preferred embodiment. The picture is taken prior to deposition of the conductive layer.
Figure 14:
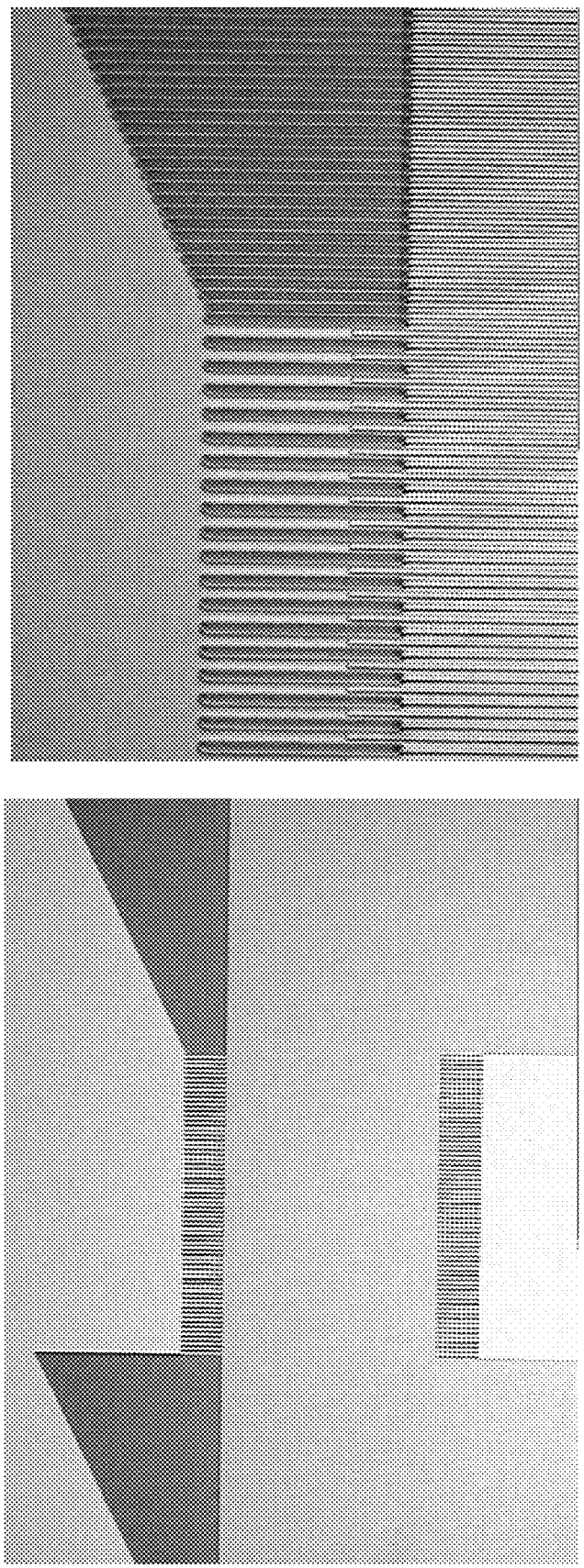
FIG. 14 shows detailed pictures of the structures of FIG. 13: left the interdigitated electrode area with part of the isolation area; right a detail of the hills and channels of the interdigitated electrode area and the isolation area.
Figure 15:
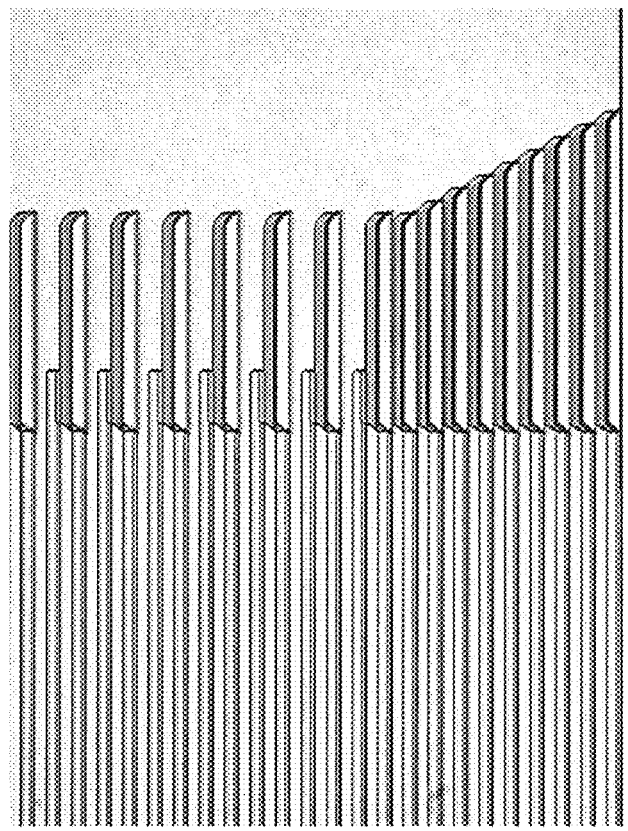
FIG. 15 shows a detailed picture of the hills and channels at the edge of the interdigitated electrode areas and the isolation area after directional deposition of a thin gold layer, visualising the shadow zones resulting from directional deposition.
Figure 16:
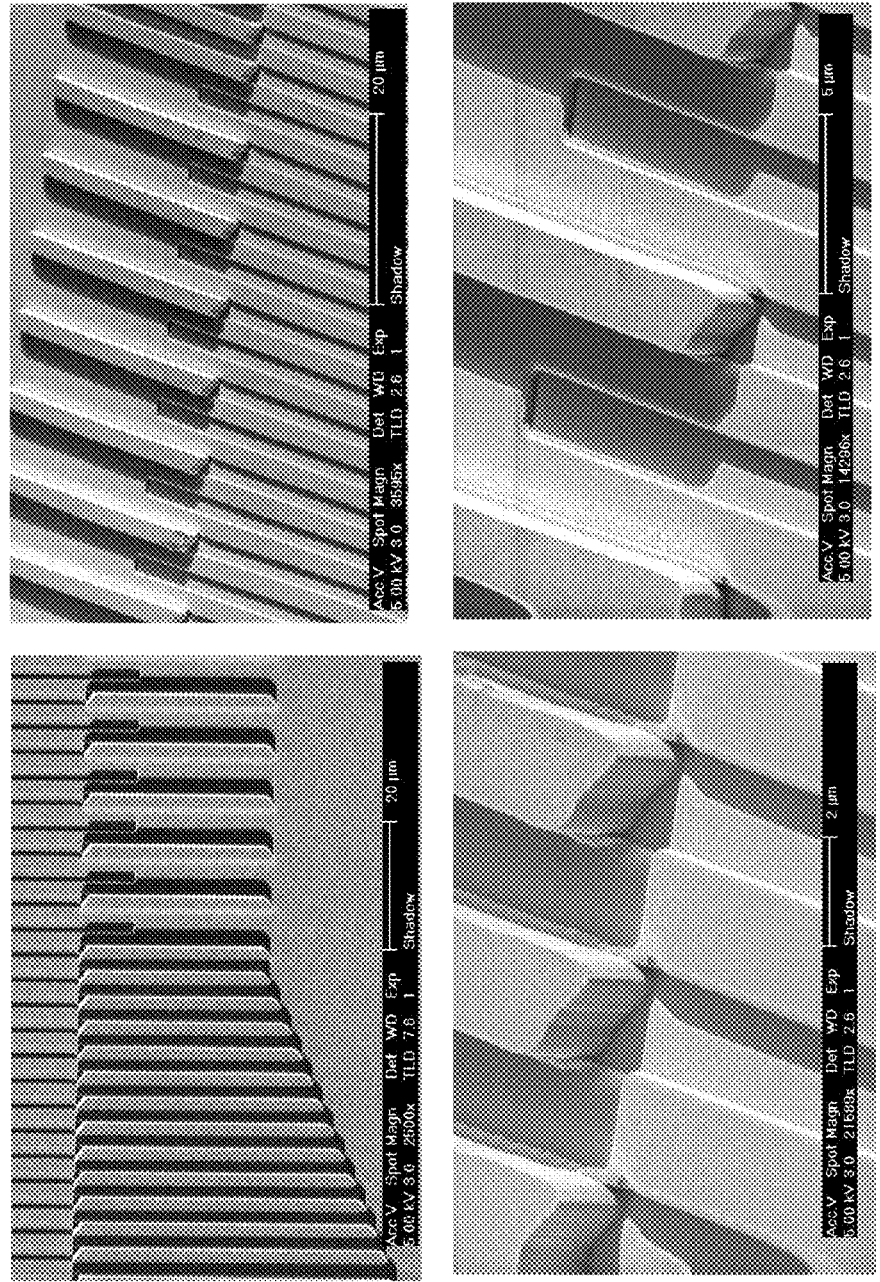
FIG. 16 shows SEM images of a preferred embodiment in a silicon wafer. At the top left, the isolation region near the electrode region is shown. At the top right a detail of hills and channels in the electrode region is shown. At the bottom a zoom of the pictures at the top is shown near the hills, clearly illustrating the shadow zones at the back side of the hills with respect of the deposition direction.

In FIG. 13, a picture taken with an optical microscope shows the three-dimensional structures in a silicon wafer of 10 electrode regions arranged in an array as described above. In FIG. 14 detailed pictures of part of the three-dimensional structures are shown prior to depositing the conductive material: left the interdigitated electrodes and part of the isolation area and right a detail of the hills and the channels of the interdigitated electrodes and hills and channels of the isolation area. In FIG. 15, a detailed picture of the interdigitated electrodes and part of the isolation area is shown after deposition of a thin gold layer. In FIG. 16, SEM-pictures show the three-dimensional structures: at the top left hills and channels at the edge of the electrode region near the isolation region; at the top right a detail of the hills in the electrode region is shown. At the bottom a zoom of the pictures at the top is shown near the hills, clearly illustrating the shadow zones near the hills and in the channels.

In the fourth aspect, an apparatus comprising an interdigitated electrode array is described. This apparatus comprises
  at least one sensor comprising interdigitated electrodes,
  means for contacting each of the first and second electrodes,
  means for applying a voltage on each of the first and second electrodes,
  means for measuring the electrical properties or the impedance between the first and second electrodes of each electrode region,
  means for applying a sample solution to be tested,
  optionally probes for binding to molecules, present in a sample to be tested. Said probes can be applied to either the insulating part of the channels and/or to the surface of the electrodes. A different probe can be applied on the individual sensors.

Figure 17:
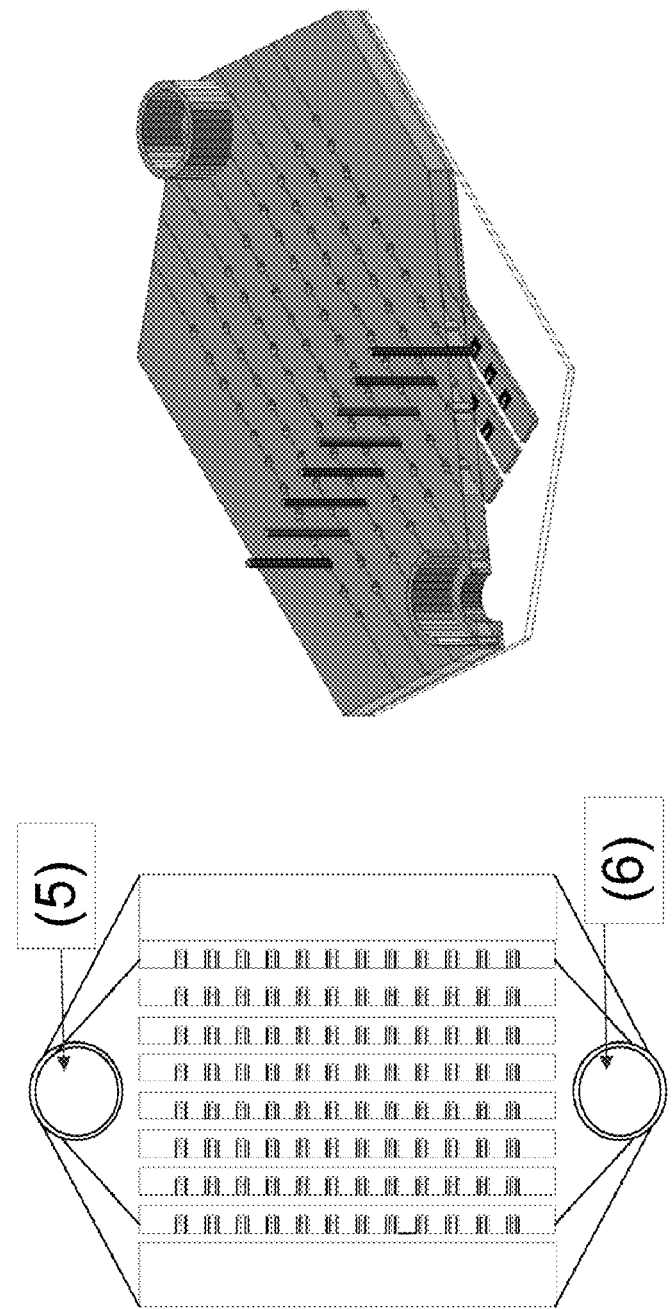
FIG. 17 shows a drawing of an interdigitated electrode array comprising 96 interdigitated electrodes on a bottom plastic plate, assembled with a cover plastic plate, bearing the micro-fluidic channels (5) and (6).

A sensor apparatus having the preferred embodiment is illustrated in FIG. 17. The interdigitated electrode array consists of 96 sensors, arranged in 8 columns and 12 rows, on a bottom plastic plate. A cover plastic plate contains the micro-fluidic channels (5) and (6). Contacting the electrodes is done through 104 holes in the plastic cover plate: 96 contacts to one electrode of each sensor+8 contacts to the electrodes connecting all sensors in a column. By applying an electrical signal, i.e. voltage or current, between the different electrodes an electric field arises, resulting in electric field lines. If molecules to be detected are present in the sample solution, they will bind to the specific probes, resulting in a change in the electric field when compared to the field without this molecular structure. This change in electrical field can be detected by measuring the impedance at the proper frequency and/or dc bias. By preference this electrical measurement is an impedance analysis, which can devolve in a measurement of resistance, capacitance, dielectric loss and/or reactance over a frequency range, including or not dc bias, or a combination of these techniques.

Figure 18:
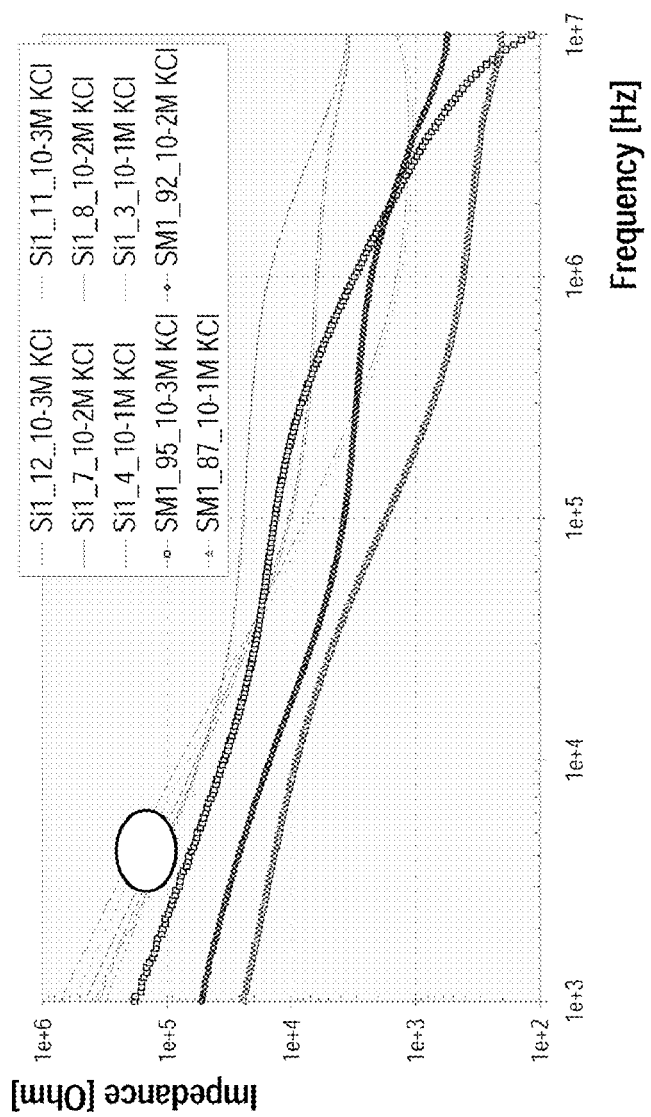
FIG. 18 shows the impedance part of the Bode plot showing the impedance characteristics of the three-dimensional structures in a silicon wafer, on which 100 nm DC-sputtered $Ta_2O_5$ was deposited as an insulating film followed by the directional deposition of Au at an angle of 80° towards the surface normal. The impedance characteristics of the interdigitated electrodes resulting from this directional metal deposition (denoted SM) are compared to the response of silicon-based planar structures realised using deep UV lithography (denoted Si). The response of both types of interdigitated electrodes is shown for several concentration of KCl (i.e. $10^{-1}$, $10^{-2}$ and $10^{-3}$M) dispensed on top of the electrodes.

FIG. 18 shows the impedance part of the Bode plot showing the impedance characteristics of the three-dimensional structures in a silicon wafer, on which 100 nm DC-sputtered $Ta_2O_5$ was deposited as an insulating film followed by the directional deposition of Au at an angle of 80° towards the surface normal. The impedance characteristics of the interdigitated electrodes resulting from this directional metal deposition (denoted SM) are compared to the response of silicon-based planar structures realised using deep UV lithography (denoted Si), which is the conventional way for processing interdigitated electrodes. The three-dimensional structures in a silicon wafer have channels with a width and spacing of 1 μm. The silicon-based planar structures realised using deep UV lithography have electrode width and spacings of 1 μm as well. In FIG. 18, the response of both types of interdigitated electrodes is shown for several concentration of KCl (i.e. $10^{-1}$, $10^{-2}$ and $10^{-3}$M) dispensed on top of the electrodes. First, the interdigitated electrodes resulting from the directional metal deposition on the three-dimensional structures in a silicon wafer do not exhibit short circuits, indicating the effectiveness of the preferred embodiment for the isolation region. Second, as also observed for the silicon-based planar structures realised using deep UV lithography, the impedimetric response of the interdigitated electrodes resulting from the directional metal deposition on the three-dimensional structures in a silicon wafer clearly changes as a function of the salt concentration, which is an indication of the formation of interdigitated electrodes to any person skilled in the art. Third, taking into account 100 nm DC-sputtered $Ta_2O_5$ is not a perfect insulator, both types of interdigitated electrodes show a similar impedimetric profile.

The invention claimed is:

1. A method for producing a sensor by non-orthogonal directional deposition of a conductive material on an insulating substrate, comprising:
   a) defining at least one electrode region on said insulating substrate, each having a first zone for forming a first electrode, a second zone for forming a second electrode, and an intermediate zone where the first and the second zones overlap, for forming interdigitated fingers of the first and the second electrodes;
   b) defining at least one isolation region for forming three-dimensional isolation structures adjacent each of said electrode regions, each of said isolation regions being located outside the adjacent electrode region and extending at least on opposite sides of the first zone of the adjacent electrode region;
   c) forming isolation structures in each of said isolation regions, said structures being shaped for creating shadow zones in which substantially no material is deposited upon directional deposition of conductive material in a predetermined deposition direction, said shadow zones providing electrical isolation between conductive material which is deposited in said first zone and conductive material which is deposited outside said first zone; and
   d) depositing a conductive material on said insulating substrate by non-orthogonal directional deposition in said predetermined deposition direction, thereby forming said first and second electrodes and said shadow zones.

2. A method according to claim 1, wherein step c) comprises forming a plurality of first interspaced channels or hills located at least along opposite sides of said first zone, said first channels or hills being located and having predetermined dimensions sufficient for maintaining electrical isolation between said first and second electrodes upon directional depositing of said conductive material.

3. A method according to claim 1, wherein step c) comprises:
   e) forming a plurality of first interspaced channels in said insulating substrate along opposite sides of said first zone; and
   f) forming first hills at the end of said channels near said second zone, said hills being sized and located such that each hill creates a shadow zone upon directional depositing the conductive material in which at least one edge of the hill of the subsequent channel is located.

4. A method according to claim 3, wherein at least one edge of said first hills in step f) is put in a tapered way such that each hill creates a shadow zone in the predetermined deposition direction in which one end of the hill of the subsequent channel is located.

5. A method according to claim 1, further comprising limiting the area wherein said conductive material is deposited such that said isolation structures extend beyond said area at least on the side of the first zone.

6. A method according to claim 5, wherein said isolation structures further extend alongside each second zone for providing electrical isolation between conductive material which is deposited in the second zone and conductive material which is deposited outside this second zone, and wherein said area in which conductive material is further limited such that said isolation structures extend beyond said area on the side of the second zone.

7. A method according to claim 1, further comprising forming an isolation structure at one edge of at least one of said first and second zones, said edge being located opposite to said intermediate zone, said structure being shaped for creating shadow zones in which substantially no conductive material is deposited during said directional deposition of conductive material, said shadow zones providing electrical isolation between conductive material which is deposited inside and outside said first or second zone.

8. A method according to claim 1, wherein step a) comprises forming a plurality of second interspaced channels or hills in said intermediate zone being located and having dimensions sufficient for maintaining electrical isolation between the fingers of said first and second electrodes upon directional depositing said conductive material.

9. A method according to claim 1, wherein step a) comprises:
   g) forming a plurality of second interspaced channels in said insulating substrate, said second channels having a predetermined depth and width sufficient for maintaining a separation between the conductive material at both sides of said channels upon directional depositing said conductive material,
   h) forming second hills at alternating ends of said second channels, said hills being sized and located such that each hill creates a shadow zone in the deposition direction in which at least the end of the subsequent channel is located such that said first and second electrodes are electrically isolated upon directional depositing said conductive material.

10. A method according to claim 2, wherein the top surfaces of at least said first or said second hills have a trapezoidal shape, said trapezoidal top surfaces having two edges parallel to the direction of the channel regions, the shortest of said parallel edges located at the side of the shadow zone of said hill.

11. A method according to claim 1, wherein:
step c) comprises forming a plurality of first interspaced channels or hills located at least along opposite sides of said first zone, said first channels or hills being located and having predetermined dimensions sufficient for maintaining electrical isolation between said first and second electrodes upon directional depositing of said conductive material;
step a) comprises forming a plurality of second interspaced channels or hills in said intermediate zone being located and having dimensions sufficient for maintaining electrical isolation between the fingers of said first and second electrodes upon directional depositing said conductive material; and
said second channels have essentially the same direction as said first channels, wherein the number of said first channels is in the range between 50 and 250, and wherein the number of said second interspaced channels is in the range between 100 and 250.

12. A method according to claim 1, wherein:
step c) comprises forming a plurality of first interspaced channels or hills located at least along opposite sides of said first zone, said first channels or hills being located and having predetermined dimensions sufficient for maintaining electrical isolation between said first and second electrodes upon directional depositing of said conductive material;
step a) comprises forming a plurality of second interspaced channels or hills in said intermediate zone being located and having dimensions sufficient for maintaining electrical isolation between the fingers of said first and second electrodes upon directional depositing said conductive material; and
said interspaced channels have a height and a width in the same order of magnitude, said height and width chosen between 1 μm and 5 μm.

13. A method according to claim 1, wherein a shadow mask is used for locally depositing said conductive material.

14. A method according to claim 1, wherein said conductive material is chosen from the group comprising Au, Ag, Pt, Pd, Cu, Al, Ta, Ti, and Indium Tin oxide (ITO).

15. A method according to claim 1, wherein said conductive material is deposited with a method chosen from the group comprising physical vapor deposition (PVD), self-ionized plasma (SIP) deposition, e-beam evaporation, and thermal evaporation.

16. A method according to claim 1, wherein said non-orthogonal directional deposition of conductive material is performed at an angle in the range between 60° and 85° with respect to the normal on the insulating substrate.

17. A method according to claim 1, wherein said insulating substrate including said three-dimensional structures are polymer replicas formed by molding using mold inserts.

18. A method according to claim 17, wherein said mould inserts are manufactured by electroplating or Galvano forming a reverse copy of a master structure.

19. A method according to claim 18, wherein said master structure is made of silicon using microelectronics patterning techniques.

20. A method according to claim 1, wherein said insulating substrate is made from a material chosen from the group consisting of polysulfon (PSU), cyclo olefin copolymer (COO), or polyphenylene (PPS).

21. A method according to claim 1, further comprising applying probes to the insulating part of the channels or to the surface of electrodes, the probes being operative to bind to molecules present in a sample to be tested.

22. A method according to claim 21 wherein the probes are chosen from the group consisting of peptides, enzymes, antigens, antibodies, oligonucleotides, DNA, and RNA, said probes being covalently or non-covalently attached to said sensor.

* * * * *